US007198891B2

(12) United States Patent
Branch et al.

(10) Patent No.: US 7,198,891 B2
(45) Date of Patent: Apr. 3, 2007

(54) HEPATITIS C VIRUS PEPTIDES AND USES THEREOF

(76) Inventors: Andrea D. Branch, 923 5th Ave., New York, NY (US) 10021; Jose L. Walewski, 95 Tuckahoe Ave., Eastchester, NY (US) 10709; Decherd D. Stump, 529 E. 83rd St., Apt. 5R, New York, NY (US) 10028

( * ) Notice: Subject to any disclaimer, the term of this patent is extended or adjusted under 35 U.S.C. 154(b) by 576 days.

(21) Appl. No.: 10/601,020

(22) Filed: Jun. 20, 2003

(65) Prior Publication Data
US 2004/0156862 A1    Aug. 12, 2004

Related U.S. Application Data

(62) Division of application No. 09/719,277, filed as application No. PCT/US99/12929 on Jun. 9, 1999, now Pat. No. 7,052,830.

(60) Provisional application No. 60/089,138, filed on Jun. 11, 1998, provisional application No. 60/088,670, filed on Jun. 9, 1998.

(51) Int. Cl.
C12Q 1/70    (2006.01)
(52) U.S. Cl. ........................................................ 435/5
(58) Field of Classification Search ..................... None
See application file for complete search history.

(56) References Cited

U.S. PATENT DOCUMENTS

| | | | |
|---|---|---|---|
| 5,350,671 A | 9/1994 | Houghton et al. | 435/5 |
| 5,443,965 A | 8/1995 | Reyes et al. | 435/693 |
| 5,728,520 A | 3/1998 | Weiner et al. | 435/5 |
| 5,840,839 A | 11/1998 | Wang et al. | 530/325 |
| 5,922,532 A * | 7/1999 | Deleys et al. | 435/5 |
| 6,027,729 A | 2/2000 | Houghton et al. | 424/228.1 |
| 6,054,264 A | 4/2000 | Chien et al. | 435/5 |
| 6,074,846 A | 6/2000 | Ralston et al. | 435/69.3 |
| 6,150,087 A | 11/2000 | Chien | 435/5 |
| 6,171,782 B1 | 1/2001 | Houghton et al. | 435/5 |
| 7,052,830 B1 * | 5/2006 | Branch et al. | 435/5 |

FOREIGN PATENT DOCUMENTS

| | | |
|---|---|---|
| WO | WO 94/25601 A2 | 11/1994 |
| WO | WO 94/25601 A3 | 11/1994 |
| WO | WO 96/05315 A2 | 2/1996 |
| WO | WO 96/05315 A3 | 2/1996 |
| WO | WO 96/40227 A1 | 12/1996 |

OTHER PUBLICATIONS

Walewski et al., RNA, 2002, vol. 8, p. 557-571.*
Walewski et al., RNA, 2001, vol. 7, p. 710-721.*
Boulani, S. et al "Unusual multiple recoding events leading to alternative forms of hepatitis C virus core protein fom Genotype 1b." *J Biol Chem.* Nov. 14, 2003: 278(46).45785-92.
Branch, A D, et al "The hepautus C virus alternate reading frame (ARF) and its family of novel products the alternate reading frame protein/F-protein, the double-frameshift protein, and others." *Semin Liver Dis* Feb. 25, 2005(1) 105-17.
Choi, J et al "Triple decoding of hepatitis C virus RNA by programmed translational frameshifting." *Mol Call Biol.* Mar. 23, 2003(5). 1489-97.
Komurian-Pradel, F., et al "Antigenic relevance of F protein in chronic hepatitis C virus infection, " *Hepatology.* Oct. 2004 40(4) 900-9.
Ogata, S, et al "Comparative sequence analysis of the core protein and its frameshift product, the F protein, of hepatitis C virus subtype 1b strains obtained from patients with and without hepatocellular carcinoma." *J Clin Microbiol.* Oct. 2002 40(10):3625-30.
Rodriguez-Lopes, M. "Immunogenecity of variable regions of hepatitis C proteins " *Journ. Of Gen. Virol.* 1999, BO 727-73.
Roussel, J., et al. "Characterization of expression of the Hepatitis C virus F protein" *J virol* 2003, 84 1751-1759.
Tan. S-L., et al. "Hepatitis C therapeutics current status and emerging strategies." *Nature* Nov. 1, 2002 867-881.
Vassilaki, N et al. "Two alternative translation mechanisms are responsible for the expression of the HCV ARFT/F/Core +1 coding open reading frame" *J Biol Chem.*Oct. 2003 278 40503-40513.
Walewski, J.L., et al. "Reading between the lines evidence for a new Hepatitis C virus protein." *Hepatology.*Sep. 2003 36(3) 757-60.
Walewski, J L, et al "Mutation Master profiles of substitutions in hepatitis C virus RNA of the core, alternate reading frame, and NS2 coding regions," *RNA.* May 8, 2002(5). 557-71.
Walewski, J.L., et al. "Evidence for a new hepatitis C virus antigen encoded in an overlapping reading frame." *RNA.* May 7, 2001(5). 710-21.
Walewski, J L, et al. "HCV patients have antibodies against a novel protein encoded in a second reading frame." *Hepatology* 28(4, Pt. 2):278A, Abstr. 462 (Oct. 1998).
Xu. Z., et al. "Hepatitis C virus F protein is a short-lived protein associated with the endoplasmic reticulum" *J Virol.* Jan. 2003; 77(2):1578-83.
Yeh, C-T, et al. "Amino acid substitutions in codons 9-11 of hepatitis C virus core protein lead to the synthesis of a short core protein product." *J Gastroenterol Hepatol.* Feb. 2000; 15(2) 182-91.
Bullock, T.N.J. et al., "Ribosomal scanning past the primary initiation codon as a mechanism for expression of CTL epitopes encoded in alternative reading frames," *J. Exp. Med.*, 184:1319-29 (1996).
Feucht, H.-H. et al. "Study on Reliability of Commercially Available Hepatitis C Virus Antibody Tests" *Journal of Clinical Microbiology* 33(3):620-624 (Mar. 1995).
Ina, Y. et al. "Reduction of synonymous substitutions in the core protein gene of hepatitis C virus," *J. Mol. Evol.*, 38:50-56 (1994).
Lo, S.-Y. et al. "Comparative studies of the core gene products of two different hepatitis C virus isolates: two alternative forms determined by a single amino acid substitution". *Virology* 199(1):124-31(Feb. 15, 1994).

(Continued)

Primary Examiner—Stacy B. Chen
Assistant Examiner—Agnieszka Boesen
(74) Attorney, Agent, or Firm—Lahive & Cockfield, LLP

(57) ABSTRACT

Novel hepatitis C virus (HCV) polypeptides are provided which are not encoded by the standard HCV open reading frame. These alternate reading frame polypeptides are useful, inter alia, in vaccine compositions, in diagnosing HCV infection, and as therapeutic targets.

39 Claims, No Drawings

OTHER PUBLICATIONS

Lo, S.-Y. et al. "Differential subcellular localization of hepatitis C virus core gene products." *Virology* 213(2):455-61(Nov. 10, 1995).

Lo, S.-Y. et al. "Interaction between hepatitis C virus core protein and E1 envelope protein." *J. Virol.* 70(8):5177-82 (Aug. 1996).

Malarkannan, S. et al. "Presentation of out-of-frame peptide/MHC class 1 complexes by a novel translation initiation mechanism." *Immunity* 10(6):681-90 (Jun. 1999).

Ray, B.R et al. "Hepatitis C virus core protein cooperates with ras and transforms primary rat embryo fibroblasts to tumorigenic phenotype." *J. Virol.* 70(7):4438-43 (Jul. 1996).

Smith, D. B. et al. "Characteristics of nucleotide substitution in the hepatitis C virus genome: Constraints on sequence change in coding regions at both ends of the genome." *J. Mol. Evol.*, 45:238-246 (1997).

Valenzuela, P. et al. "The nucleotide sequence of the hepatitus B viral genome and the identification of the major viral genes. " in *Animal Virus Genetics*, Academic Press, pp. 57-70 (1980).

Varaklioti, A. et al. "Alternate translation occurs with the core coding region of the Hepatitis C viral genome." *Journal of Biological Chemistry* 277(20):17713-21 (2002).

Walewski, J.L. et al. "A western blot assay for detection of patient antibodies to an HCV alternate reading frame protein." *Abstract in Hepatology* 30(4):41A poster 163 (1999).

Walewski, J.L. et al. "HCV Patients Have Antibodies Against a Novel Protein Encoded in a Second Reading Frame." *Hepatology* 28(4, Pt. 2):278A, Abstr. 462 (Oct. 1998).

Wang, J. et al. "Proteolytic conversion of hepatitis B virus e antigen precursor to end product occurs in a postendoplasmic reticulum compartment." *J. Virol.* 65:5080-83 (Sep. 1991).

Xu, Z. et al. "Synthesis of a novel hepatitis C virus protein by ribosomal frameshift." *EMBO J.* 20(14):3840-48 (2001).

* cited by examiner

US 7,198,891 B2

HEPATITIS C VIRUS PEPTIDES AND USES THEREOF

RELATED APPLICATIONS

This application is a divisional application of Ser. No. 09/719,277 filed Apr. 13, 2001 now U.S. Pat. No. 7,052,830, which is the U.S. National Stage of PCT/US99/12929, International filing date Jun. 9, 1999, now pending, which claims priority to U.S. Ser. No. 60/088,670, filed 9 Jun. 1998 and to U.S. Ser. No. 60/089,138, filed 11 Jun. 1998. The contents of all the aforementioned application(s) are hereby incorporated by reference.

GOVERNMENT FUNDING

This work was funded, in part, by NIH grants DK 50795 and DK 52071. The government may, therefore, have certain rights to this invention.

BACKGROUND OF THE INVENTION

Hepatitis C virus (HCV) is closely related to both the pestivirus and flavivirus genera in the Flaviviridae family. HCV is a single stranded RNA virus; the viral genome is approximately 9.5 kb. HCV RNA is positive sense and has a unique open reading frame which encodes a single polyprotein (Clarke. 1997. *J. Gen. Virol.* 78:2397). The polyprotein is proteolyticly processed to yield the mature viral proteins which include: nucleocapsid, envelope 1, envelope 2, metalloprotease, serine protease, RNA helicase, cofactor, and RNA polymerase.

HCV is a major human pathogen. The virus was found to be the cause of most cases of hepatitis which could not be ascribed to hepatitis A, hepatitis B, or hepatitis delta virus (Clarke, supra). Over fifty percent of patients with hepatitis C virus (HCV) become chronic carriers of the virus; there may be as many as 500 million chronic carriers worldwide (Dhillon and Ducheiko. 1995. *Histopathology* 26: 297). Persistent infection with the virus causes chronic hepatitis and may ultimately lead to cirrhosis and/or cancer (Kuo et al. 1989. *Science* 244:362). Current therapies for HCV are ineffective, consequently there is a need for new approaches to treat HCV infection.

SUMMARY

The present invention is an important advance in the battle against hepatitis C. The novel peptides of the invention, which are not encoded by the standard, polyprotein HCV reading frame, have been shown to elicit an immune response in patients infected with HCV and, thus, are produced during HCV infection. Accordingly, the invention provides novel HCV polypeptides which are not derived from the HCV polyprotein and methods of their use.

In one aspect, the invention pertains to an isolated or recombinant polypeptide or fragment thereof encoded by a nucleic acid molecule derived from a hepatitis C virus, which polypeptide has at least one of the following characteristics:

1) at least a portion of the polypeptide is encoded by a reading frame +1 or +2 relative to the standard hepatitis C virus open reading frame;

2) at least a portion of the polypeptide is encoded by a reading frame corresponding to the reading frame of SEQ ID NO:1 in which the first nucleotide of SEQ ID NO:1 is the first nucleotide of a codon;

3) at least a portion of the polypeptide comprises an amino acid sequence at least 60% identical to the amino acid sequence shown in SEQ ID NO:2; and 4) at least a portion of the polypeptide comprises an amino acid sequence encoded by a nucleic acid molecule which hybridizes under high stringency to the nucleotide sequence shown in SEQ ID NO:1.

In certain embodiments of the invention the novel HCV polypeptides or portion thereof of claim 1 are at least about 8 amino acids to at least about 100 amino acids in length. In other embodiments, the polypeptides or portions thereof are at least about 14 amino acids to at least about 30 amino acids in length.

In one embodiment, the novel HCV polypeptides or portions thereof are encoded by a reading frame +1 or +2 to the standard hepatitis C reading frame. In preferred embodiments, the polypeptides are encoded by a reading frame corresponding to the reading frame of SEQ ID NO:1 in which the first nucleotide of SEQ ID NO:1 is the first nucleotide of a codon. In other preferred embodiments, the polypeptides are encoded, in part by the nucleic acid molecule of SEQ ID NO:1 and cause an immune response in a subject.

In other embodiments, the novel HCV polypeptides comprise an amino acid sequence at least 60% identical to the amino acid sequence shown in SEQ ID NO:2 and cause an immune response in a subject. In preferred embodiments, the novel HCV polypeptides comprise an amino acid sequence at least 90% identical to the amino acid sequence shown in SEQ ID NO:2 and causes an immune response in a subject. In other preferred embodiments, the novel HCV polypeptides comprise an amino acid sequence shown in SEQ ID NO: 2 and cause an immune response in a subject.

In other embodiments, the novel HCV polypeptides comprise an amino acid sequence encoded by a nucleic acid molecule which hybridizes under high stringency to the nucleotide sequence shown in SEQ ID NO:1.

In other embodiments, the novel HCV polypeptides comprise at least a portion of an amino acid sequence selected from the group consisting of SEQ ID NO: 3, SEQ ID NO:4, SEQ ID NO:5, SEQ ID NO:6, SEQ ID NO:7, and SEQ ID NO:8 and cause an immune response in a subject.

In still other embodiments, the invention pertains to isolated or recombinant polypeptides comprising an amino acid sequence selected from the group consisting of: LNLKEKP(X1)(X2)TPT(X3) and AAHRT(X4)SSR(X5)(X6)VR, wherein X1 is N or K, X2 is V or E, X3 is A or V, X4 is L or S, X5 is A or V, and X6 is A or V. In yet other embodiments, the novel HCV polypeptides consist of an amino acid sequence selected from the group consisting of LNLKEKPNVTPTAC and AAHRTSSSRAVVRC.

In another aspect, the invention pertains to a vaccine composition for preventing hepatitis C infection in a subject. In one embodiment such a vaccine comprises a novel HCV polypeptide. In another embodiment, such a vaccine comprises a nucleic acid encoding a novel HCV polypeptide.

In another aspect, the invention pertains to an antibody which binds to a novel HCV polypeptide.

In yet another aspect the invention pertains to a kit for detecting a hepatitis C infection. In one embodimetn, such a kit comprises a novel HCV polypeptide. In another aspect, the kit comprises an antibody which binds to a novel HCV polypeptide.

In yet another aspect, the invention pertains to a method of preventing HCV infection by administering a novel HCV polypeptide to a subject or by causing said polypeptide to be synthesized is a subject prior to HCV infection such that HCV infection is prevented.

The invention also pertains to methods of diagnosing HCV infection. In one embodiment, the method comprises detecting the presence or absence of antibodies which react with a novel HCV polypeptide in the body fluid of a subject, wherein the presence of antibodies which bind the polypeptide is indicative of an infection with HCV. In another embodiment, the method comprises detecting the presence or absence of a novel HCV polypeptide in the body fluid or tissue of a subject, wherein the presence of an HCV polypeptide is indicative of an infection with HCV.

In still another aspect, the invention pertains to a method for identifying a compound which interacts with a novel HCV polypeptide by contacting the polypeptide with a compound in a cell-free system under conditions which allow interaction of the compound with the polypeptide such that a complex is formed; separating the compounds which do not form complexes with an HCV polypeptide from those which do form complexes with an HCV polypeptide; and isolating and identifying the compounds which form complexes with an HCV polypeptide to identify a compound which interacts with a novel HCV polypeptide.

DETAILED DESCRIPTION

The present invention is an important step forward in preventing Hepatitis C (HCV) infection, in treating ongoing infection, and in improving existing diagnostic techniques. The invention is based, in part, on the identification of novel polypeptides encoded by the Hepatitis C viral genome. These novel polypeptides are not encoded by the standard HCV polyprotein reading frame.

Before further description of the invention, certain terms employed in the specification, examples and appended claims are, for convenience, collected here.

I. Definitions

As used herein, the language "isolated or recombinant polypeptide" includes a polypeptide which is substantially free of cellular material or culture medium when produced by recombinant DNA techniques, or chemical precursors or other chemicals when chemically synthesized.

As used herein, the term "polypeptide or fragment thereof" includes full-length polypeptide molecules (from the first amino acid of translation initiation to the last amino acid prior to translation termination) and peptide portions of such molecules. Preferably the novel HCV polypeptides or fragments thereof are at least about 8 amino acids to at least about 100 amino acids in length. More preferably the polypeptides or fragments thereof are at least about 14 amino acids to at least about 30 amino acids in length. In preferred embodiments, the novel HCV polypeptides of the invention comprise an amino acid sequence which is conserved among different HCV isolates. Such a conserved sequence can readily be determined using an alignment such as that provided in Table 1. In other embodiments, the novel HCV polypeptides comprise a portion of a novel HCV amino acid sequence which is distal (carboxy terminal) to a stop codon in the +1 reading frame (relative to the main ORF) that includes the "UG" of the "AUG" that is the initiator codon of the main ORF. In a more preferred embodiment, the polypeptides or fragments thereof cause an immune response in a subject.

As used herein, the language "nucleic acid molecule" is intended to include DNA molecules (e.g., cDNA or genomic DNA) and RNA molecules (e.g., genomic viral RNA or mRNA). The nucleic acid molecule may be single-stranded or double-stranded.

As used herein, the language "the standard hepatitis C virus open reading frame" is the open reading frame (ORF) of the viral RNA which encodes the well-known HCV polyprotein. The standard ORF represents the largest ORF in the viral genome. In the infectious clone (GenBank accession number AF011751) the standard ORF uses nucleotide 342 as the first nucleotide of a codon and continues until nucleotide 9377. In different HCV isolates, the nucleotide which is a first nucleotide of a codon of the standard ORF may be at a slightly different position. The nucleotide which is a first nucleotide of a codon for any isolate can be easily be obtained to yield the standard HCV ORF. For example, in the case of known isolates GenBank (or another database containing the nucleotide sequence information for the isolate) can be accessed and the coding sequence (CDS) information can be obtained. Alternatively, to determine the standard ORF of a known or a new isolate, the nucleic acid sequence of the known or new isolate can be aligned with a known sequence to give the highest homology (e.g., using a program such as BLAST). An exemplary BLAST search can be done, e.g., using the sequence found in GenBank accession number AF011751, as the query sequence. In this search, nucleotides 342–940 of AF011751 were used to search the non-redundant sequence database. The ORF of other HCV isolates which corresponds to the standard HCV ORF of AF011751 (in which the initiation codon is at position 342, which is read as position 1 of the query sequence) can be read from the BLAST alignment. For example, the corresponding first nucleotide of a codon for GenBank accession no. HPCCGAA is 342. Another way to find the standard ORF would be to use a program, such as Edit Seq. (DNASTAR) which is designed to identify ORFS using the AUG aligned with position 342 of AF011751 as the start codon.

The term "percent (%) identity" as used in the context of nucleotide and amino acid sequences (e.g., when one amino acid sequence is said to be X % identical to another amino acid sequence) refers to the percentage of identical residues shared between the two sequences, when optimally aligned. To determine the percent identity of two nucleotide or amino acid sequences, the sequences are aligned for optimal comparison purposes (e.g., gaps may be introduced in one sequence for optimal alignment with the other sequence). The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity=# of identical positions/total # of positions× 100).

Computer algorithms known in the art can be used to optimally align and compare two nucleotide or amino acid sequences to define the percent identity between the two sequences. A preferred, non-limiting example of a mathematical algorithm utilized for the comparison of two sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs of Altschul, et al. (1990) J. Mol. Biol. 215:403–10. To obtain gapped alignments for comparison purposes, Gapped BLAST can be utilized as described in Altschul et al., (1997) Nucleic Acids Research 25(17):3389–3402. When utilizing BLAST and Gapped BLAST programs, the default parameters of the respective programs (e.g., XBLAST and NBLAST) can be used.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. If multiple programs are used to compare sequences, the program that provides optimal alignment (i.e., the highest percent identity between the two sequences) is used for comparison purposes.

As used herein, the language "+1 or +2 relative to the standard hepatitis C virus open reading frame" includes reading frames in which a first nucleotide of a codon is shifted +1 nucleotide relative to the standard ORF or +2 nucleotide relative to the standard ORF. The reading frames encoding the novel polypeptides do not necessarily contain an in-frame start codon.

As used herein, the language "the reading frame of SEQ ID NO:1" means that the first three nucleotides of the sequence shown in SEQ ID NO:1 are the first second and third nucleotides of a codon for translation into an amino acid of a polypeptide. The reading frame of SEQ ID NO:1 is +1 relative to the standard HCV ORF. The language "a reading frame corresponding to the reading frame of SEQ ID NO:1" means that when a sequence from an HCV isolate other than the AF011751 isolate shown in SEQ ID NO:1 is aligned with the sequence of SEQ ID NO:1 to give the highest homology, e.g., using the BLAST program, it is then read in the same reading frame as SEQ ID NO:1 to give the reading frame corresponding the reading frame of SEQ ID NO:1. The nucleotide position of a first nucleotide of a codon of an HCV isolate which corresponds to that of SEQ ID NO:1 may vary from isolate to isolate. An exemplary BLAST search illustrating this principle is provided as Appendix B. For example, for GenBank accession number AF009606 a first nucleotide of a codon in a reading frame which corresponds to the reading frame of SEQ ID NO:1 is nucleotide 346.

As used herein, the term "hybridizes under high stringency" is intended to describe conditions for hybridization and washing under which nucleotide sequences at least 70% homologous to each other typically remain hybridized to each other. Preferably, the conditions are such that sequences at least 75%, 85%, or 95% identical to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C.

As used herein, the term "antibody" is intended to include immunoglobulin molecules and immunologically active portions of immunoglobulin molecules, i.e., molecules that contain an antigen binding site which specifically binds (immunoreacts with) an antigen, such as Fab and F(ab')$_2$ fragments. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody compositions thus typically display a single binding affinity for a particular antigen with which it immunoreacts.

As used herein, the term "adjuvant" includes agents which potentiate the immune response to an antigen. Adjuvants can be administered in conjunction with the subject polypeptides to additionally augment the immune response.

As used herein, the term "enhancing an immune response" includes increasing T and/or B cell responses, i.e., cellular and/or humoral immune responses, by treatment of a subject using the claimed methods. In one embodiment, the claimed methods can be used to enhance T helper cell responses. In another embodiment, the claimed methods can be used to enhance cytotoxic T cell responses. The claimed methods can be used to enhance both primary and secondary immune responses. Preferably, the immune response is increased as compared to the response of immune cells to the antigen in the absence of treatment with the claimed methods. The immune response of a subject can be determined by, for example, assaying antibody production, immune cell proliferation, the release of cytokines, the expression of cell surface markers, cytotoxicity, enchanced ability to clear infection with HCV, etc.

II. Novel HCV Polypeptides

The novel HCV polypeptides of the invention are not derived from an HCV polyprotein, i.e., the polypeptides of the present invention are not encoded by the standard HCV ORF. These alternate reading frame polypeptides are translated from (or synthesized based on) a reading frame which is +1 or +2 to the standard HCV ORF. The position of the first nucleotide of an ORF in which these polypeptides are translated will vary slightly depending upon the isolate studied. For example, for the infectious clone (GenBank accession number AF011751) the first nucleotide of the ORF in which the novel HCV polypeptides are translated is nucleotide 346, which is +5 relative to the standard HCV ORF. The first nucleotide of a codon of other, known or new isolates which results in a reading frame which corresponds to the reading frame of SEQ ID NO:1 can be determined, e.g., by performing a BLAST search using the nucleic acid sequence of SEQ ID NO:1 as the query sequence as described above.

Translation of the novel HCV polypeptides of the invention does not necessarily have to begin at a start AUG codon. For example, previous work has shown that the start AUG of HCV could be mutated to AUU or CUG with little effect on translation efficiency (Clarke, supra). Alternatively, RNA editing may be involved in generating an initiator codon. Translation of the novel HCV polypeptides may also begin at the initiation site of the standard HCV ORF with a frame shift into a different reading frame. Finally, translation may be initiated 5' of the AUG start codon of the standard ORF in any of the three reading frames, but shifted into the +1 reading frame (relative to the standard ORF) so as to yield production of peptides which are, in part, at least 60% identical to a portion of SEQ ID NO. 2. The internal ribosome entry site (IRES) is a complex RNA structural element that includes part of the 5' untranslated region of HCV RNA and part of the adjacent coding region. It may induce frame shifting or translational by passing.

In preferred embodiments, the polypeptides are encoded by a reading frame corresponding to the reading frame of SEQ ID NO:1 in which the first nucleotide of SEQ ID NO:1 is the first nucleotide of a codon. This reading frame can encode a polypeptide of at least about 126 amino acids in length before a termination codon is reached. Table 1 presents an alignment of novel HCV polypeptides which are encoded in this reading frame from various HCV isolates, along with a majority sequence derived using the Clustal method of sequence alignment. Stop codons appear in certain of the isolates after amino acid 126. However, translation may proceed beyond these stop codons. For example, in certain cases, these stop codons may be sequencing errors. Alternatively, readthrough can occur by mutation, altered transcription, RNA editing, frame shifting or ribosome slippage. Therefore, even in the polypeptides in which a stop codon appears, in certain embodiments of the invention, the novel HCV polypeptide may be longer, i.e., translation may proceed past a termination codon. Therefore, in the case of, e.g., the infectious clone AF011751, translation of the polypeptide could terminate, for example, at position 163 or 186 of SEQ ID NO:2. When the novel HCV polypeptides of the invention are synthesized, these stop codons may be ignored.

In other embodiments, the polypeptides of the invention have some percentage identity to the sequence shown in SEQ ID NO:2. The percent identity between two nucleic acid or amino acid sequences can easily be calculated by dividing the number of identical bases or amino acids by the total number of bases or amino acids. Sequences are aligned to give the highest percent identity and yet provide an alignment which is biologically meaningful. Sequences can be aligned manually or, preferably, using an algorithm. For example, in the case of amino acid sequences, a FASTA search can be performed of the Swiss Protein database using the Biosum50.Cmp (scoring matrix). The gap creation penalty can be set, e.g., at 12 and the extension penalty can be set e.g., at 2. The joining threshold can be set, e.g., at 36; the optimization threshold can be set, e.g., at 24; and the optimization width can be set, e.g., at 16.

In certain embodiments, the novel HCV polypeptides comprise an amino acid sequence at least about 40–50% identical to the amino acid sequence shown in SEQ ID NO:2. In preferred embodiments, the novel HCV polypeptides comprise an amino acid sequence at least about 50–60% identical to the amino acid sequence shown in SEQ ID NO:2. In other preferred embodiments, the novel HCV polypeptides comprise an amino acid sequence at least about 60–70% identical to the amino acid sequence shown in SEQ ID NO:2. In more preferred embodiments, the novel HCV polypeptides comprise an amino acid sequence at least about 70–80% identical to the amino acid sequence shown in SEQ ID NO:2. In still more preferred embodiments, the novel HCV polypeptides comprise an amino acid sequence at least about 80–90% identical to the amino acid sequence shown in SEQ ID NO:2. In another preferred embodiment, the novel HCV polypeptides comprise an amino acid sequence shown in SEQ ID NO:2.

In preferred embodiments, the polypeptides of the invention have the described percent identity over a length of at least about 10 amino acids. In more preferred embodiments, the percent identity of the polypeptides extends over a length of at least about 20–30 amino acids. In more preferred embodiment, the percent identity of the polypeptides extends over a length of at least about 30–40 amino acids. In a more preferred embodiment, the percent identity of the polypeptides extends over a length of at least about 40–50 amino acids. In another more preferred embodiment, the percent identity of the polypeptides extends over a length of more than 50 amino acids. In other embodiments, the percent identity of the polypeptides extends over a length of more than 100 amino acids.

In other embodiments, the novel HCV polypeptides comprise an amino acid sequence encoded by a nucleic acid molecule having some percentage identity to the nucleic acid molecule shown in SEQ ID NO:1. In certain embodiments, the novel HCV polypeptides comprise an amino acid sequence encoded by a nucleic acid molecule at least 70% identical shown in SEQ ID NO:1 in which the polypeptide is encoded by the reading frame shown in SEQ ID NO:1. In preferred embodiments, the novel HCV polypeptides comprises an amino acid sequence encoded by a nucleic acid molecule at least 80% identical shown in SEQ ID NO:1 in which the polypeptide is encoded by the reading frame shown in SEQ ID NO:1. In more preferred embodiments, the novel HCV polypeptides comprise an amino acid sequence encoded by a nucleic acid molecule at least 90% identical shown in SEQ ID NO:1 in which the polypeptide is encoded by the reading frame shown in SEQ ID NO:1. In other embodiments, novel HCV polypeptides comprise an amino acid sequence encoded by a nucleic acid molecule shown in SEQ ID NO:1 in which the polypeptide is encoded by the reading frame shown in SEQ ID NO:1.

In certain embodiments, the novel HCV polypeptides of the invention are encoded by a nucleic acid molecule which hybridizes under stringent conditions to the nucleic acid sequence shown in SEQ ID NO:1. Stringent hybridization conditions are known in the art. In preferred embodiments, such polypeptides are encoded by a nucleic acid molecule which hybridizes under stringent conditions to a nucleic acid molecule from any HCV isolate, but which are read in or synthesized as if read in the reading frame of SEQ ID NO:1.

In other embodiments, the novel HCV polypeptides comprise at least a portion of an amino acid sequence selected from the group consisting of SEQ ID NO: 3, SEQ ID NO:4, SEQ ID NO:5, SEQ ID NO:6, SEQ ID NO:7, and SEQ ID NO:8 and cause an immune response in a subject. Other novel HCV polypeptides can be identified using an HCV nucleic acid sequence and determining the amino acids which are encoded in the +1 or +2 reading frame. Polypeptides of comprising these sequences can be made and assayed for reactivity with antibodies from infected subjects. Those polypeptides which bind to antibodies, i.e., have elicited an immune response in infected subjects are made by the virus during the course of infection and represent preferred novel HCV polypeptides.

In still other embodiments, the invention pertains to isolated or recombinant polypeptides comprising an amino acid sequence selected from the group consisting of: LNLKEKP(X1)(X2)TPT(X3) (SEO ID NO:3) and AAHRT(X4)SSR(X5)(X6)VR (SEQ ID NO:4), wherein X1 is N or K, X2 is V or E, X3 is A or V, X4 is L or S, X5 is A or V, and X6 is A or V. In yet other embodiments, the novel HCV polypeptides consist of an amino acid sequence selected from the group consisting of LNLKEKPNVTPTAC (SEQ ID NO:5) and AAHRTSSSRAVVRC (SEQ ID NO:6).

In certain embodiments of the invention the novel HCV polypeptides of the invention are at least about 8 amino acids to at least about 100 amino acids in length. In other embodiments, the polypeptides of the invention are at least about 10 amino acids to at least about 50 amino acids in length. In other embodiments, the polypeptides of the invention are at least about 14 to at least about 25 amino acids in length.

In preferred embodiments, the novel HCV polypeptides are of a length sufficient to cause an immune response in a subject. Such an immune response can be measured using techniques which are known in the art. For example, the immune response elicited by the HCV polypeptides of the invention can be a T cell-mediated response which can be measured by, e.g., cytokine production and/or cellular proliferation or cellular cytotoxicity and/or a B cell mediated response which can be measured, e.g., by antibody production.

In certain embodiments the novel HCV polypeptides of the invention are made as fusion proteins. In addition to utilizing fusion proteins to enhance immunogenicity, fusion proteins can also facilitate the expression of proteins, including the novel HCV polypeptides of the present invention. For example, a the novel HCV polypeptide can be generated as a glutathione-S-transferase (GST-fusion protein). Such GST-fusion proteins can enable easy purification of the novel HCV polypeptide, as for example by the use of glutathione-derivatized matrices (see, for example, *Current Protocols in Molecular Biology*, eds. Ausubel et al. (N.Y.: John Wiley & Sons, 1991)). In another embodiment, a fusion gene coding for a purification leader sequence, such as a poly-(His)/enterokinase cleavage site sequence, can be can be fused to a the novel HCV polypeptide, in order to permit purification of the poly(His)-the novel HCV polypeptide by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

It will be understood that the preceding characteristics of HCV polypeptides are not mutually exclusive.

III. Production of Novel HCV Polypeptides

Novel HCV polypeptides can be produced by recombinant DNA techniques. For example, a nucleic acid molecule encoding such a polypeptide is cloned into an expression vector, the expression vector is introduced into a host cell and the novel HCV polypeptide is expressed in the host cell. The novel HCV polypeptide can then be isolated from the cells by an appropriate purification scheme using standard protein purification techniques. As an alternative to recombinant expression, a novel HCV polypeptide can be synthesized chemically using standard peptide synthesis techniques or purchased commercially. Moreover, native novel HCV polypeptides can be isolated from cells (e.g., cultured human cells infected with HCV), for example using an antibody.

A. Recombinant Production of Novel HCV Polypeptides

In certain embodiments, the novel HCV polypeptides are encoded by a naturally-occurring HCV nucleic acid molecule. As used herein, a "naturally-occurring" nucleic acid molecule refers to an RNA molecule (or a DNA molecule derived therefrom) having a nucleotide sequence that occurs in nature (e.g., encodes a protein produced by a naturally occurring HCV isolate).

In addition to naturally-occurring isolates of the novel HCV polypeptides, the skilled artisan will further appreciate that changes may be introduced by mutation, e.g., into an HCV nucleotide sequence thereby leading to changes in the amino acid sequence of the encoded HCV polypeptides.

For example, an isolated nucleic acid molecule encoding a novel HCV polypeptide homologous to the polypeptide of SEQ ID NO: 2, i.e., having a certain percentage identity to the polypeptide of SEQ ID NO:2 can be created by introducing one or more nucleotide substitutions, additions or deletions into the nucleotide sequence of SEQ ID NO: 1 such that one or more amino acid substitutions, additions or deletions are introduced into the encoded polypeptide. Mutations can be introduced into SEQ ID NO: 1 by standard techniques, such as site-directed mutagenesis and PCR-mediated mutagenesis. Alternatively, such a polypeptide can be chemically synthesized to yield a polypeptide with a change in amino acid sequence from that in the naturally occurring polypeptide.

Preferably, no substitutions or conservative amino acid substitutions are made where the is high homology or identity in amino acid residues among the various isolates. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Alternatively, in another embodiment, mutations can be introduced randomly along all or part of a novel HCV polypeptide coding sequence, such as by saturation mutagenesis, and the resultant mutants can be screened, e.g., by testing for reactivity with antibodies from an individual with a past or present HCV infection.

B. Expression Vectors and Host Cells

The nucleic acid molecules described herein can be expressed in an expression vector to produce a novel HCV polypeptide. As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid molecule as described herein in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequencers) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce novel HCV polypeptides, including fusion proteins comprising such polypeptides.

The recombinant expression vectors of the invention can be designed for expression of novel HCV polypeptides in prokaryotic or eukaryotic cells. For example, novel HCV polypeptides can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nuc. Acids Res.* 20:2111–2118). Such alteration of nucleic acid sequences of the invention can be carried out by standard DNA synthesis techniques.

In another embodiment, the novel HCV polypeptides expression vector is a yeast expression vector. Examples of vectors for expression in yeast *S. cerivisae* include pYepSec1 (Baldari. et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, novel HCV polypeptides can be expressed in insect cells using baculovirus expression vectors. Baculovirus vectors available for expression of proteins in cultured insect cells (e.g., Sf 9 cells) include the pAc series (Smith et al., (1983) *Mol. Cell Biol.* 3:2156–2165) and the pVL series (Lucklow, V. A., and Summers, M. D., (1989) *Virology* 170:31–39).

In yet another embodiment, a nucleic acid molecule encoding novel HCV polypeptides of the invention is expressed in mammalian cells using a mammalian expression vector. Examples of mammalian expression vectors include pCDM8 (Seed, B., (1987) *Nature* 329:840) and pMT2PC (Kaufman et al. (1987), *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

A recombinant expression vector is introduced into a suitable host cell. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences such progeny may not, in fact, be identical to the parent cell, but are still included within the scope of the term as used herein.

A host cell may be any prokaryotic or eukaryotic cell. For example, novel HCV polypeptides may be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual,* 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same vector as that encoding the polypeptide or may be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) novel HCV polypeptides. Accordingly, the invention further provides methods for producing novel HCV polypeptides using these host cells. In one embodiment, the method comprises culturing the host cell of invention (into which a recombinant expression vector encoding novel HCV polypeptides has been introduced) in a suitable medium until a novel HCV polypeptide is produced. In another embodiment, the method further comprises isolating novel HCV polypeptides from the medium or the host cell.

C. Chemical Synthesis of Novel HCV Polypeptides

The novel HCV polypeptides can be chemically synthesized as is well known in the art. Moreover, the peptide can be substituted and/or derivatized to optimize stability. The subject polypeptides can also be synthesized as branched polypeptides, particularly for vaccine applications as is known in the art (see, e.g., Peptides. Edited by Bernd Gutte Academic Press 1995. pp. 456–493).

IV. Antibodies Which React With Novel HCV Polypeptides

In yet another aspect, the invention pertains to an antibody which binds to a novel HCV polypeptide. A novel HCV polypeptide, or fragment thereof, can be used as an immunogen to generate antibodies that bind such a polypeptide using standard techniques for polyclonal and monoclonal antibody preparation. The invention provides numerous antigenic peptide fragments of novel HCV polypeptides for use as immunogens. Preferably, an antigenic peptide of such a polypeptide comprises at least 8 amino acid residues of the amino acid sequence shown in SEQ ID NO: 2 or the ARF #1 polypeptide or ARF #2 polypeptide consensus sequences. Preferably, the antigenic peptide comprises at least 10 amino acid residues, more preferably at least 14 amino acid residues, even more preferably at least 18 amino acid residues. Preferred polypeptides comprise the ARF #1 consensus sequence :LNLKEKP(X1)(X2)TPT(X3) (SEQ ID NO:3) or the ARF#2 consensus sequence AAHRT(X4)SSR(X5)(X6) VR (SEQ ID NO:4), wherein X1 is N or K, X2 is V or E, X3 is A or V, X4 is L or S, X5 is A or V, and X6 is A or V polypeptide sequences. Other preferred HCV polypeptides compnse or consist of the sequence LNLKEKPNVTPTAC (SEQ ID NO:5) or AAHRTSSSRAVVRC (SEQ ID NO:6).

The subject HCV polypeptides are used to prepare antibodies by immunizing a suitable subject, (e.g., rabbit, goat, mouse or other mammal) with the immunogen. An appropriate immunogenic preparation can contain, for example, recombinantly expressed novel HCV polypeptides or a chemically synthesized novel HCV polypeptide can be used. The preparation can further include an adjuvant, such as Freund's complete or incomplete adjuvant, or similar immunostimulatory agent. Immunization of a suitable subject with an immunogenic HCV polypeptides preparation induces a polyclonal HCV polypeptides antibody response.

Accordingly, another aspect of the invention pertains to antibodies which react with the novel HCV polypeptides. The term "antibody" as used herein refers to immunoglobulin molecules and immunologically active portions of immunoglobulin molecules, i.e., molecules that contain an antigen binding site which specifically binds (immunoreacts with) an HCV polypeptides. The invention provides polyclonal and monoclonal antibodies that bind HCV polypeptides. The term "monoclonal antibody" or "monoclonal antibody composition", as used herein, refers to a population of antibody molecules that contain only one species of an antigen binding site capable of immunoreacting with a particular epitope of a novel HCV polypeptide. A monoclonal antibody composition thus typically displays a single binding affinity for a particular HCV polypeptide with which it reacts.

Polyclonal anti-HCV polypeptide antibodies can be prepared as described above by immunizing a suitable subject with a HCV polypeptide immunogen or attenuated HCV virus, or can be obtained from an infected individual. The anti-HCV polypeptide antibody titer in the immunized subject can be monitored over time by standard techniques, such as with an enzyme linked immunosorbent assay (ELISA) using immobilized HCV polypeptide. If desired, the antibody molecules directed against HCV polypeptide can be isolated from the animal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975, *Nature* 256:495–497) (see also, Brown et al. (1981) *J. Immunol* 127:539–46; Brown et al. (1980) *J Biol Chem* 255:4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.*, 3:231–36). Briefly, an immortal cell line (typically a myeloma) is fused to lymphocytes (typically splenocytes) from a mammal immunized with a HCV polypeptide immunogen as described above, and the culture supernatants of the resulting hybridoma cells are screened to identify a hybridoma producing a monoclonal antibody that binds the HCV polypeptide.

Any of the many well known protocols used for fusing lymphocytes and immortalized cell lines can be applied for the purpose of generating an anti-HCV polypeptide monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed).

Hybridoma cells producing a monoclonal antibody of the invention are detected by screening the hybridoma culture supernatants for antibodies that bind HCV polypeptides, e.g., using a standard ELISA assay.

Alternative to preparing monoclonal antibody-secreting hybridomas, a monoclonal anti-HCV polypeptide antibody can be identified and isolated by screening a recombinant combinatorial immunoglobulin library (e.g., an antibody phage display library) with HCV polypeptides to thereby isolate immunoglobulin library members that bind HCV polypeptides. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffiths et al. (1993) *EMBO J* 12:725–734; Hawkins et al. (1992) *J Mol Biol* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; Barbas et al. (1991) *PNAS* 88:7978–7982; and McCafferty et al. *Nature* (1990) 348:552–554.

Additionally, recombinant anti-HCV polypeptide antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira, et al. European Patent Application 184,187; Taniguchi, M., European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-HCV polypeptide antibody (e.g., monoclonal antibody) can be used to isolate or detect HCV polypeptides by standard techniques, such as affinity chromatography, immunoprecipitation, ELISA, or RIA as is well known in the art. An anti-HCV polypeptide antibody can facilitate the purification of natural HCV polypeptide from cells and of recombinantly produced HCV polypeptides expressed in host cells. Moreover, an anti-HCV polypeptide antibody can be used to detect HCV polypeptides from a body fluid of a subject which is suspected to have an HCV infection. Detection may be facilitated by coupling (i.e., physically linking) the antibody to a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^3$H.

Such antibodies can be incorporated in diagnostic kits and are also useful in passive immunization against HCV in patients which have an active HCV infection or are likely to be exposed to HCV.

IV. Uses of Novel HCV Polypeptides

In another aspect, the invention pertains to a vaccine composition which is administered to a subject prior to exposure to HCV to preventing hepatitis C infection in the subject. In one embodiment, the vaccine comprises a novel HCV polypeptide of the invention. In another embodiment, the vaccine causes a novel HCV polypeptide of the invention to be synthesized in a subject.

A. Vaccines

Novel HCV polypeptide sequences appropriate for use in vaccine compositions for the prevention of HCV in a subject can easily be determined. For example, epitopes which elicit an immune response can be identified by screening in an immunoassay against sera from patients with a past or ongoing HCV infection. Alternatively, immunogenic polypeptides can be identified by computer analysis to identify immunogenic epitopes. Finally, the full-length novel polypeptide could be used in a vaccine.

In another embodiment, agents which are known adjuvants can be administered with the subject polypeptides. At this time, the only adjuvant widely used in humans has been alum (aluminum phosphate or aluminum hydroxide). Saponin and its purified component Quil A, Freund's complete adjuvant and other adjuvants used in research and veterinary applications have potential use in human vaccines. However, new chemically defined preparations such as muramyl dipeptide, monophosphoryl lipid A, phospholipid conjugates such as those described by Goodman-Snitkoff et al. J. Immunol. 147:410–415 (1991) resorcinols, non-ionic surfactants such as polyoxyethylene oleyl ether and n-hexadecyl polyethylene ether, enzyme inhibitors include pancreatic trypsin inhibitor, diisopropylfluorophosphate (DEP) and trasylol can also be used. In embodiments in which antigen is administered, the antigen can e.g., be encapsulated within a proteoliposome as described by Miller et al., J. Exp. Med. 176:1739–1744 (1992) and incorporated by reference herein, or in lipid vesicles, such as Novasome™ lipid vesicles (Micro Vascular Systems, Inc., Nashua, N.H.), to further enhance immune responses.

In yet other embodiments, as an alternative to administering the novel HCV polypeptide, the polypeptide can be synthesized by the subject. This can be done using a plasmid DNA construct which is similar to those used for delivery of reporter or therapeutic genes. Such a construct preferably comprises a bacterial origin of replication that allows amplification of large quantities of the plasmid DNA; a prokaryotic selectable marker gene; a nucleic acid sequence encoding a novel HCV polypeptide or portion thereof; eukaryotic transcription regulatory elements to direct gene expression in the host cell; and a polyadenylation sequence to ensure appropriate termination of the expressed mRNA (Davis. 1997. Curr. Opin. Biotechnol. 8:635). Vectors used for DNA immunization may optionally comprise a signal sequence (Michel et al. 1995. Proc. Natl. Acad. Sci USA. 92:5307; Donnelly et al. 1996. J. Infect Dis. 173:314). DNA vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al. 1996. J. Biotechnol. 44:37)). Alternatively, DNA vaccines can be administered by non-invasive means. For example, pure or lipid-formulated DNA can be delivered to the respiratory system or targeted elsewhere, e.g., Peyers patches by oral delivery of DNA (Schubbert. 1997. Proc. Natl. Acad. Sci. USA 94:961). Attenuated microorganisms can be used for delivery to mucosal surfaces. (Sizemore et al. 1995. Science. 270:29)

Any of the instant vaccine compositions can comprise (or encode) one or more epitopes (either contiguous or non contiguous) of a novel HCV polypeptide. Such preparations can further comprise polypeptide sequences derived from an HCV polyprotein sequence. In other embodiments, such a vaccine composition can further comprise a compound which will enhance the immunologocial reactivity of the novel HCV polypeptide epitope. For example, the immunogenicicty of the novel HCV polypeptides may be enhanced by making a fusion proteins comprising a novel HCV polypeptide fused to a different polypeptide, i.e., not a novel HCV polypeptide. Techniques for making such fusion proteins are known in the art. Alternatively, a vaccine can comprise an immunoregulatory molecule, such as a cytokine. For example, in one embodiment, plasmids for DNA vaccination can express a single immunogen, or two sequences can be coexpressed. In one embodiment, the additional sequences can be additional immunogens (novel HCV polypeptides or HCV polyprotein polypeptides or other polypeptides) or can encode modulators of immune responses such as lymphokine genes or costimulatory molecules (Iwasaki et al. 1997. J. Immunol. 158:4591)

Typically, vaccine compositions of the present invention are prepared as injectables, either as liquid solutions or suspensions. Solid forms suitable for solution in, or suspension in, liquid prior to injection may also be prepared. The composition may also be emulsified, or the polypeptide encapsulated into liposomes. The polypeptide may be mixed with pharmaceutically acceptable excipients, for example, water, saline, dextrose, glycerol, ethanol, or the like. The composition may also comprise minor amounts of, for example, wetting agents, pH buffering agents and/or adjuvants, such as aluminum hydroxide, N-acetyl-muramyl-L-threonyl-D-isoglutamine (thr-MDP), N-acetyl-nor-muramyl-L-alanyl-D-isoglutamine (CGP 11637 or nor-MDP), N-acetylmuramlyl-L-alanyl-D-isoglutaminyl-L-alanine-2-(1'-2'-dipalmitoyl-sn-glycerol-3-hydroxyphosphoryloxy) ethylamine (CGP 19835A, or MTP-PE), or bacterial components.

Such vaccine compositions are generally administered parenterally, by injection, usually wither subcutaneously or intramuscularly. Other formulations may be administered orally, by inhalation or as suppositories.

The polypeptides may be incorporated into the vaccine in a neutral or salt form. Pharmaceutically acceptable salts include the acid addition salts (formed with free amino groups of the polypeptide) and which are formed with inorganic acids, such as, for example, hydrochloric or phosphoric acids, or such organic acids such as acetic, oxalic, tartaric, maleic, or the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, or the like.

The vaccines are administered so as to be compatible with the dosage formulation, and in such an amount as will be prophylactically and/or therapeutically effective. The quantity to be administered depends on the subject to be treated, the capacity of the subject's immune system to mount an immune response to the vaccine, and the degree of protection desired. The range of 5 µg to 250 µg of antigen per dose, however, is often appropriate. The vaccine compositions may be given in a single dose or in multiple doses. Appropriate doses are well within the skill of the art to determine, and do not constitute undue experimentation.

In still another embodiment, the invention pertains to a method of preventing HCV in a subject by administering a novel HCV polypeptide to a subject or by causing a novel HCV polypeptide to be expressed in a subject.

B. Diagnostic Kits

In another aspect of the invention, methods for diagnosing HCV infection e.g., either a past or present infection, and diagnostic kits are provided for detecting an infection with HCV.

In one embodiment, the invention provides a method of diagnosing HCV infection by detecting the presence or absence of antibodies in the body fluid of a subject which bind to a novel HCV polypeptide. In one embodiment the method comprises incubating a test sample under conditions which allow the binding of a novel HCV polypeptide and an antibody in the test sample of body fluid and detecting the binding of polypeptide and antibody.

Test samples can be derived from any appropriate body fluid or tissue preparation, for example, whole blood, plasma, serum, spinal fluid, lymph fluid, tears, saliva, milk, or liver tissue preparations.

Detection of the binding between a novel HCV polypeptide of the invention and an antibody can be accomplished using any technique which is known in the art and can be facilitated using antibodies labelled as described above.

Antibodies which bind to novel HCV polypeptide can be detected using a number of different screening assays known in the art, such as an enzyme-linked immunosorbent assay (ELISA), a radioimmunoassay (RIA), or a Western Blot Assay. Each assay generally detects the presence of protein-antibody complexes of particular interest by employing a labeled reagent (e.g., an antibody) specific for the complex of interest. Accordingly, in the present invention, these assays are used to detect novel HCV polypeptide-antibody complexes formed between immunoglobulins (e.g., human IgG, IgM and IgA) contained in a biological sample and a novel HCV polypeptide. As will be described below, these protein-antibody complexes are preferably detected using an enzyme-linked antibody or antibody fragment (e.g., a monoclonal antibody or fragment thereof) which recognizes and specifically binds to the polypeptide-antibody complexes.

In one embodiment of the method, a sandwich ELISA assay is used. For example, a novel HCV polypeptide with or without conjugation to a carrier, such as activated BSA is immobilized on a plate. A body fluid sample from an individual is contacted with a novel HCV polypeptide under conditions which allow binding of the antibodies in the sample to the polypeptides. The sample is then removed, and any antibody which has bound to the HCV polypeptide is detected by contacting the sample with a labeled secondary antibody or antibody fragment which binds to an antibody which might be present in the subjects sample, e.g., an anti-human antibody. The unbound secondary antibody is removed and the presence of secondary antibody which remains bound is detected, e.g., using a label as described above. Possible controls for use in the method include body fluids from uninfected subjects and polypeptides which are not novel HCV polypeptides. In accordance with the present invention, the presence of such an antibody is indicative of an infection with HCV.

In another embodiment of the assay the test sample can be tested for the presence of novel HCV polypeptides using known antibodies. In these embodiments, antibodies that bind to novel HCV polypeptides are used to detect the presence of novel HCV polypeptides in the body fluid of a subject or in a cell of a subject. In performing such an assay, the antibodies which bind to a novel HCV polypeptide are contacted with a cell or body fluid of a subject under conditions where a novel HCV polypeptide in the subject's sample can bind to the antibody. Unbound antibody is removed and bound antibody is detected. Any of the antibodies described above can be used in practicing this method. Preferred antibodies for use in the methods of this embodiment are highly specific, including monospecific and, more preferably, monoclonal antibodies or fragments thereof. In preferred embodiments, such antibodies are labelled. In other embodiments, such antibodies are detected by employing a secondary antibody which binds to them and not to the test sample from a subject. The presence of a novel HCV polypeptide in the subject's sample is indicative of an infection with HCV.

In yet another aspect, the present invention provides an assay kit for diagnosing HCV infection in a subject. Preferably, the kit contains a solid support (e.g., an ELISA plate) capable of adsorbing immunoglobulin (e.g., IgG, IgM and IgA) from a subject's sample (preferably a human biological sample, such as a body fluid) and a monoclonal antibody or fragment thereof specific for a novel HCV polypeptide. In another embodiment, the solid support can be omitted from the kit. In another embodiment, the kit contains a solid support (e.g., an ELISA plate or a slide) and a monoclonal antibody or fragment thereof specific for a novel HCV polypeptide. In other embodiments, the solid support can be omitted. The assay kit can optionally include instructions, or additional reagents such as a solution for washing unbound proteins from the solid support, and materials needed for performing a detection assay.

C. Targets for Therapeutic Intervention

The novel HCV polypeptides of the invention are also targets for anti-HCV therapy. As such the invention provides methods for identifying compounds which interact with a novel HCV polypeptide and, thus, are likely to interfere with infection. In one embodiment, the method involves contacting the polypeptide with a compound in a cell-free system under conditions which allow interaction of the compound with the polypeptide such that a complex is formed. The complexes of polypeptide and compound can then be separated from the compounds which do not bind to the HCV polypeptide, the compounds which bind to HCV polypeptides can then be isolated and identified.

Exemplary compounds which can be screened for activity in the subject assays include, but are not limited to, peptides, nucleic acids, carbohydrates, small organic molecules, and natural product extract libraries. The term "non-peptidic compound" is intended to encompass compounds that are comprised, at least in part, of molecular structures different from naturally-occurring L-amino acid residues linked by natural peptide bonds. However, "non-peptidic compounds" are intended to include compounds composed, in whole or in part, of peptidomimetic structures, such as D-amino acids, non-naturally-occurring L-amino acids, modified peptide backbones and the like, as well as compounds that are composed, in whole or in part, of molecular structures unrelated to naturally-occurring L-amino acid residues linked by natural peptide bonds. "Non-peptidic compounds" also are intended to include natural products.

A recent trend in medicinal chemistry includes the production of mixtures of compounds, referred to as libraries. While the use of libraries of peptides is well established in the art, new techniques have been developed which have allowed the production of mixtures of other compounds, such as benzodiazepines (Bunin et al. 1992. J. Am. Chem. Soc. 114:10987; DeWitt et al. 1993. Proc. Natl. Acad. Sci. USA 90:6909) peptoids (Zuckermann. 1994. J. Med. Chem. 37:2678) oligocarbamates (Cho et al. 1993. Science. 261: 1303), and hydantoins (DeWitt et al. supra). Rebek et al. have described an approach for the synthesis of molecular libraries of small organic molecules with a diversity of 104–105 (Carell et al. 1994. Angew. Chem. Int. Ed. Engl. 33:2059; Carell et al. Angew. Chem. Int. Ed. Engl. 1994. 33:2061).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. Anticancer Drug Des. 1997. 12:145).

In one embodiment, the test compound is a peptide or peptidomimetic. In another, preferred embodiment, the compounds are small, organic non-peptidic compounds.

Other exemplary methods for the synthesis of molecular libraries can be found in the art, for example in: Erb et al. 1994. Proc. Natl. Acad. Sci. USA 91:11422; Horwell et al. 1996 Immunopharmacology 33:68; and in Gallop et al. 1994. J. Med. Chem. 37:1233.

Libraries of compounds may be presented in solution (e.g., Houghten (1992) Biotechniques 13:412–421), or on beads (Lam (1991) Nature 354:82–84), chips (Fodor (1993) Nature 364:555–556), bacteria (Ladner U.S. Pat. No. 5,223, 409), spores (Ladner U.S. Pat. No. '409), plasmids (Cull et al. (1992) Proc Natl Acad Sci USA 89:1865–1869) or on phage (Scott and Smith (1990) Science 249:386–390); (Devlin (1990) Science 249:404–406); (Cwirla et al. (1990) Proc. Natl. Acad. Sci. 87:6378–6382); (Felici (1991) J. Mol. Biol. 222:301–310); (Ladner supra.).

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Accordingly, in an exemplary screening assay of the present invention, the compound of interest is contacted with a novel HCV polypeptide. Detection and quantification of novel HCV polypeptide/compound complexes identifies the compound as a potential modulator of a novel HCV polypeptide. The efficacy of the compound can be assessed by generating dose response curves from data obtained using various concentrations of the test compound. Moreover, a control, e.g., using a different polypeptide can also be performed to provide a baseline for comparison.

Complex formation between the novel HCV polypeptide and a compound may be detected by a variety of techniques. For instance, modulation of the formation of complexes can be quantitated using, for example, detectably labelled proteins such as radiolabelled, fluorescently labelled, or enzymatically labelled novel HCV polypeptides, by immunoassay, or by chromatographic detection.

Typically, it will be desirable to immobilize either the novel HCV polypeptide or the compound or both to facilitate separation of compound/novel HCV complexes from uncomplexed forms, as well as to accommodate automation of the assay. In one embodiment, a fusion protein can be provided which adds a domain that allows the polypeptide to be bound to a matrix. For example, glutathione-S-transferase/receptor (GST/receptor) fusion protein forms of the novel polypeptides can be adsorbed onto glutathione sepharose beads (Sigma Chemical, St. Louis, Mo.) or glutathione derivatized microtitre plates, which are then combined with the test compound which is bound to beads and incubated under conditions conducive to complex formation, e.g. at physiological conditions for salt and pH, though slightly more stringent conditions may be desired, e.g., at 4° C. in a buffer containing 0.6M NaCl or a detergent such as 0.1% Triton X-100. Following incubation, the uncomplexed forms are removed by washing and compounds which bind to novel HCV polypeptides are identified.

Other techniques for immobilizing proteins on matrices are also available for use in the subject assay. For instance, the novel HCV polypeptides can be immobilized utilizing conjugation of biotin and streptavidin. For instance, biotinylated novel HCV polypeptides can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the novel HCV polypeptides can be derivatized to the wells of the plate, and the novel HCV polypeptides trapped in the wells by antibody conjugation. As above, preparations of a novel HCV polypeptide and a test compound are incubated in the wells of the plate, and the amount of novel HCV polypeptides/compound complex trapped in the well can be quantitated.

Other exemplary methods for detecting such complexes, in addition to those described above for the GST-immobilized complexes, include immunodetection of complexes using antibodies reactive with the novel HCV polypeptide, or which are reactive with the receptor protein and compete for binding with the novel HCV polypeptide; as well as enzyme-linked assays which rely on detecting an enzymatic activity associated with the novel HCV polypeptide. In the instance of the latter, the enzyme can be chemically conjugated or provided as a fusion protein with the novel HCV polypeptide. To illustrate, the novel HCV polypeptide can be chemically cross-linked or genetically fused with alkaline phosphatase, and the amount of novel HCV polypeptide trapped in the complex can be assessed with a chromogenic substrate of the enzyme, e.g. paranitrophenylphosphate. Likewise, a fusion protein comprising the novel HCV polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as the anti-novel HCV antibodies described herein, can be used. Alternatively, the protein to be detected in the complex can be "epitope tagged" in the form of a fusion protein which includes, in addition to the novel HCV polypeptide, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharamacia, N.J.).

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, *Genetics; Molecular Cloning A Laboratory Manual*, 2nd Ed., ed. by Sambrook, J. et al. (Cold Spring Harbor Laboratory Press (1989)); *Short Protocols in Molecular Biology*, 3rd Ed., ed. by Ausubel, F. et al. (Wiley, N.Y. (1995)); *DNA Cloning*, Volumes I and II (D. N. Glover ed., 1985); *Oligonucleotide Synthesis* (M. J. Gait ed. (1984)); Mullis et al. U.S. Pat. No. 4,683,195; *Nucleic Acid Hybridization* (B. D. Hames & S. J. Higgins eds. (1984)); the treatise, *Methods In Enzymology* (Academic Press, Inc., N.Y.); *Immunochemical Methods In Cell And Molecular Biology* (Mayer and Walker, eds., Academic Press, London (1987)); *Handbook Of Experimental Immunology*. Volumes I–IV (D. M. Weir and C. C. Blackwell, eds. (1986)); and Miller, J. *Experiments in Molecular Genetics* (Cold Spring Harbor Press, Cold Spring Harbor, N.Y. (1972)).

The contents of all references, pending patent applications and published patents, cited throughout this application are hereby expressly incorporated by reference. Specifically, the contents of U.S. Ser. No. 60/088,670, titled Novel Hepatitis C Virus Peptides And Uses Thereof, filed on Jun. 9, 1998 and Ser. No. 60/089,138, titled Novel Hepatitis C Virus Peptides And Uses Thereof, filed on Jun. 11, 1998 are incorporated herein by this reference.

The invention is further illustrated by the following examples, which should not be construed as further limiting.

EXAMPLES

Example 1

The Detection of Antibodies Against Novel HCV Polypeptides

Consensus polypeptides were synthesized based on the sequence homology between novel HCV polypeptides shown in Table 1. The following peptides were made using conventional techniques by Biosynthesis Corp. (Lewisville, Tex.): LNLKEKPNVTPTAC and AAHRTSSSRAVVRC (alternate reading frame (ARF) polypeptides 1 and 2, respectively). The following polypeptides derived from HCV CORE protein were used as controls: PTDPRRRSRNLGKVIDTC and GCATRKTSERSQPRGRRAPI. The peptides were conjugated to activated bovine serum albumin giving up to 4 peptide molecules for each BSA molecule. Peptide-BSA conjugates at a concentration of approximately 0.5 mg/ml were shipped on ice in 3 mls of phosphate buffered saline, 0.1 M, pH 7.4. They were aliquoted and stored at −20° C. until use.

ELISAs were performed as described by Kirkegaard and Perry Laboratories, Inc. (Gaithersburg, Md.). For use in the ELISA, the polypeptides were dissolved in 1× "coating buffer" to give a peptide-BSA concentration of 1 µg/ml; 100 µl were added to 96 well microtiter plates (Falcon 3072, Becton Dickinson and Company, Franklin Lakes, N.J.) and incubated at room temperature for 1 hour or overnight at 4° C. The coating solution was removed and plates were then blocked by adding 300 µl of 1% BSA in phosphate buffered saline (as prepared by Kirkegaard and Perry), and incubating for 30 min. at room temperature. The blocking solution was removed and 100 µl of 1% BSA (1×) was added.

Sera was obtained from patients which were known to have or to have previously had an HCV infection. Serum samples were diluted 1:100 in 1× BSA and 100 µl was added to the first well of each (yielding a total of 200 µl). Serum samples were then serially diluted (two-fold at each step). Control wells contained BSA only. Plates were incubated for 1 hour at room temperature with moderate agitation to allow binding. Plates were washed 5 times with 1× wash solution (PBS and 0.02% Tween). After washing, 100 µl of the secondary antibody was immediately added and allowed to react for 1 hour at room temperature. The secondary antibody was either the Fab fragment of anti-human IgG conjugated to horse radish peroxidase (HRP) at a dilution of 1:1000, or anti-human IgG (in PBS with 1% BSA). Plates were washed 5 times with 1× washing solution, and then 100 µl of hydrogen peroxide and TMB were added and allowed to react for 10 to 30 minutes at room temperature. To stop the reaction, 100 µl of 1M phosphoric acid were added. O.D. measurements were obtained by using a dual wavelength scanner: 450 nm values-650 nm values.

| Results of ELISA Tests for Antibodies of HCV-Specific Polypeptides | | |
|---|---|---|
| | Control Sera Mean OD (S.D.) (N = 2, tested in duplicate) | HCV Patient Sera Mean OD (S.D.) (N = 6, tested in duplicate) |
| CORE #1 | 0.379 (0.063) | 0.851 (0.231) |
| CORE #2 | 0.775 (0.053) | 1.390 (0.400) |
| ARF #1 | 0.763 (0.133) | 2.286 (0.215) |
| ARF #2 | 0.401 (0.039) | 0.813 (0.813) |

Example 2

Development of a Western Blot Assay for Detecting Antibody Production to Alternate HCV Reading Frame Proteins Five micrograms of BSA-alternate reading frame peptide conjugates and appropriate contols (quenched BSA, BSA-BSA peptide conjugates) were denatured by incubating in standard Lamelli loading buffer (with beta-mercaptoethanol and SDS), at 100° C. for three minutes. Samples were then cooled and spun in a microcentrifuge prior to loading on a discontinuous 1.5 mm thick SDS-PAGE gel (4% stacking gel [pH 6.8] and 12.5% [pH 8.4] resolving gel). The running buffer was TRIS-glycine/SDS (0.1%), with an unadjusted pH of approximately 8.4.

Samples were run through the stacking gel (1 cm) for approximately 45 mins at 90 volts. After the bromophenol blue (BB) entered the resolving gel, the voltage was increased to 160 V. The gels were run for approximately 1.5 hrs, or until the BB was ⅔ of the way through the gel. After stopping the run, the gels were either stained with coomassie blue, or equlibrated for 15 minutes with the transfer buffer (1×CAPS, ph 11.0, 10% MeOH. PVDF membranes (Immobilon-P [0.45 micon pore size], were wet in 100% MeOH for 1 min, then 50:50 MeOH:double distilled water for 5 mins, and finally equilibrated with the transfer buffer. The transfer was set up in transfer buffer (filter paper, gel, PVDF membrane, and filter paper), and slipped into the BIO-RAD transfer tank. The transfer was run at 20 volts, overnight (approximately 10 hrs), at 4° C., with stirring.

After transfer, the tank was disassembled, the membrane was soaked in 100% MeOH for one minute, then allowed to air-dry. In order to visualize the efficiency of the transfer, the membranes (after re-wetting in MeOH then water) were incubated with 1% Ponceau-S red stain and rinsed in double distilled water. After scanning the image, the dye was removed in a dilute NaOH solution (1 ml saturated NaOH in 100 mls ddwater.

The membranes were then blocked in 3% NFDM (6 grams non-fat dried milk in 200 mls of 1×TBS (TRIS-buffered saline, ph 7.4), for one hour. After blocking, the membranes were rinsed in two washes of 1×TBS, 200 mls apiece.

The membranes were then incubated with the primary antibody solution 4 mls of a 1/200 dilution of patient sera in 1% NFDM in 1× TTBS (TBS with 0.025% Tween-20). This incubation lasted one hour, at 30° C., in glass with slow rotation of the tube or beaker. After this incubation, the membranes were washed three times in 200 mls of 1×TTBS.

The secondary antibody solution was 200 mls of a 1/3000 dilution of the BIO-RAD goat anti-human alkaline phosphatase conjugate, in 1% NFDM in 1×TRBS. This incubation lasted 1 hr, at 30° C., with gentle shaking.

After this incubation, the membranes were washed twice with 200 ml of 1×TTBS (5 mins apiece), and one with 200 mls of 1×TBS.

The bands were visualized with the BIO-RAD AP substrate kit (200 mls total), with gentle, occasional shaking. After visualization, the membranes were washed several times with ddwater, followed by one wash with MeOH, then air-dried and photographed or scanned.

What is claimed is:

1. A method of diagnosing Hepatitis C virus (HCV) infection, comprising contacting an isolated, purified, or synthetic polypeptide comprising an amino acid sequence of at least 8 amino acids in length which amino acid sequence is encoded by an HCV nucleic acid molecule translated in a reading frame corresponding to the reading frame of SEQ ID NO:1 and +1 to the standard HCV reading frame with a biological sample from a subject, under conditions where the polypeptide and an antibody that binds to the polypeptide present in the sample can bind, and determining the presence or absence of the antibody, wherein presence of the antibody indicates infection with HCV.

2. The method of claim 1, wherein the amino acid sequence is at least 14 amino acids in length.

3. The method of claim 1, wherein the amino acid sequence is at least at least 30 amino acids in length.

4. The method of claim 1, wherein the amino acid sequence is at least 100 amino acids in length.

5. The method of claim 1, wherein the entire polypeptide is encoded by a reading frame +1 to the standard hepatitis C reading frame.

6. The method of claim 1, wherein the amino acid sequence comprises at least 8 contiguous amino acids of SEQ ID NO:2.

7. The method of claim 1, wherein the amino acid sequence is identical to the amino acid sequence shown in SEQ ID NO:2.

8. The method of claim 1, wherein the amino acid sequence comprises at least 8 contiguous amino acids of SEQ ID NO:9.

9. The method of claim 1, wherein the amino acid sequence is selected from the group consisting of: SEQ ID NO: 3, SEQ ID NO:4, SEQ ID NO:5, and SEQ ID NO:6.

10. The method of claim 1, wherein the amino acid sequence is selected from the group consisting of: LNLKEKP(X1)(X2)TPT(X3) (SEQ ID NO:3) and AAHRT(X4)SSR(X5)(X6)VR (SEQ ID NO:4), wherein X1 is N or K, X2 is V or E, X3 is A or V, X4 is L or S, X5 is A or V, and X6 is A or V.

11. The method of claim 1, wherein the amino acid sequence is selected from the group consisting of: LNLKEKPNVTPTA (SEQ ID NO:5) and AAHRTSSSRAVVR (SEQ ID NO:6).

12. The method of claim 1, wherein the polypeptide is a fusion protein.

13. The method of claim 1, wherein translation of the polypeptide begins at the initiation site of the standard HCV open reading frame with a shift into the +1 reading frame.

14. The method of claim 1, wherein an enzyme-linked immunosorbent assay (ELISA) assay is used to detect a binding antibody in the biological sample.

15. The method of claim 1, wherein an radioimmunoassay (RIA) is used to detect a binding antibody in the biological sample.

16. The method of claim 1, wherein an western blot assay is used to detect a binding antibody in the biological sample.

17. The method of claim 1, wherein the polypeptide is immobilized on a surface.

18. The method of claim 1, wherein the polypeptide is supplied in a kit.

19. A method of diagnosing Hepatitis C virus (HCV) infection, comprising contacting an isolated, purified, or synthetic polypeptide comprising an amino acid sequence of at least 8 amino acids in length which amino acid sequence is encoded by an HCV nucleic acid molecule translated in a reading frame +1 to the standard HCV reading frame with a biological sample from a subject, under conditions where the polypeptide and an antibody that binds to the polypeptide present in the sample can bind, and determining the presence or absence of the antibody wherein presence of the antibody indicates infection with HCV.

20. The method of claim 19, wherein the amino acid sequence is at least 14 amino acids in length.

21. The method of claim 19, wherein the amino acid sequence is at least at least 30 amino acids in length.

22. The method of claim 19, wherein the amino acid sequence is at least 100 amino acids in length.

23. The method of claim 19, wherein the entire polypeptide is encoded by a reading frame +1 to the standard hepatitis C reading frame.

24. The method of claim 19, wherein the amino acid sequence comprises at least 8 contiguous amino acids of SEQ ID NO:2.

25. The method of claim 19, wherein the amino acid sequence is identical to the amino acid sequence shown in SEQ ID NO:2.

26. The method of claim 19, wherein the amino acid sequence comprises at least 8 contiguous amino acids of SEQ ID NO:9.

27. The method of claim 19, wherein the amino acid sequence is selected from the group consisting of: LNLKEKPNVTPTA (SEQ ID NO:5) and AAHRTSSSRAVVR (SEQ ID NO:6).

28. The method of claim 19, wherein the polypeptide is a fusion protein.

29. The method of claim 19, wherein translation of the polypeptide begins at the initiation site of the standard HCV open reading frame with a shift into the +1 reading frame.

30. The method of claim 19, wherein an enzyme-linked immunosorbent assay (ELISA) assay is used to detect a binding antibody in the biological sample.

31. The method of claim 19, wherein an radioimmunoassay (RIA) is used to detect a binding antibody in the biological sample.

32. The method of claim 19, wherein an western blot assay is used to detect a binding antibody in the biological sample.

33. The method of claim 19, wherein the polypeptide is immobilized on a surface.

34. The method of claim 19, wherein the polypeptide is supplied in a kit.

35. A method of diagnosing Hepatitis C virus (HCV) infection, comprising contacting an isolated, purified, or synthetic polypeptide comprising an amino acid sequence of at least 8 amino acids in length which amino acid sequence is encoded by an HCV nucleic acid molecule translated in a reading frame corresponding to the reading frame of SEQ ID NO:1 and +1 to the standard HCV reading frame, which polypeptide is immobilized on a surface, with a biological sample from a subject, under conditions where the polypeptide and an antibody that binds to the polypeptide can bind, determining the presence or absence of an antibody that binds to the polypeptide, wherein the presence or absence of the antibody is detected using a secondary antibody or fragment thereof which is detectably labeled, and wherein presence of the antibody indicates infection with HCV.

36. The method of claim 35, wherein an enzyme-linked immunosorbent assay (ELISA) assay is used to detect a binding antibody in the biological sample.

37. The method of claim 35, wherein an radioimmunoassay (RIA) is used to detect a binding antibody in the biological sample.

38. The method of claim 35, wherein an western blot assay is used to detect a binding antibody in the biological sample.

39. The method of claim 35, wherein the immobilized polypeptide is supplied in a kit.

* * * * *

SEQUENCE LISTING

<160> NUMBER OF SEQ ID NOS: 17

<210> SEQ ID NO 1
<211> LENGTH: 595
<212> TYPE: DNA
<213> ORGANISM: Hepatitis C virus

<400> SEQUENCE: 1

```
gcacgaatcc taaacctcaa agaaaaacca aacgtaacac caaccgtcgc ccacaggacg      60
tcaagttccc gggtggcggt cagatcgttg gtggagttta cttgttgccg cgcagggggcc    120 ctagattggg tgtgcgcgcg acgaggaaga cttccgagcg gtcgcaacct cgaggtagac    180
gtcagcctat ccccaaggca cgtcggcccg agggcaggac ctgggctcag cccgggtacc    240
cttggcccct ctatggcaat gagggttgcg ggtgggcggg atggctcctg tctccccgtg    300
gctctcggcc tagctggggc cccacagacc cccggcgtag gtcgcgcaat ttgggtaagg    360
tcatcgatac ccttacgtgc ggcttcgccg acctcatggg gtacataccg ctcgtcggcg    420
cccctcttgg aggcgctgcc agggccctgg cgcatgcgt ccgggttctg gaagacggcg      480
tgaactatgc aacagggaac cttcctggtt gctctttctc tatcttcctt ctggccctgc    540
tctcttgcct gactgtgccc gcttcagcct accaagtgcg caattcctcg gggct          595
```

<210> SEQ ID NO 2
<211> LENGTH: 196
<212> TYPE: PRT
<213> ORGANISM: Hepatitis C virus

<400> SEQUENCE: 2

```
Ala Arg Ile Leu Asn Leu Lys Glu Lys Pro Asn Val Thr Pro Thr Val
 1               5                  10                  15

Ala His Arg Thr Ser Ser Ser Arg Val Ala Val Arg Ser Leu Val Glu
            20                  25                  30

Phe Thr Cys Cys Arg Ala Gly Ala Leu Asp Trp Val Cys Ala Arg Arg
        35                  40                  45
```

-continued

Gly Arg Leu Pro Ser Gly Arg Asn Leu Glu Val Asp Val Ser Leu Ser
            50              55                  60

Pro Arg His Val Gly Pro Arg Ala Gly Pro Gly Leu Ser Pro Gly Thr
 65              70                  75                  80

Leu Gly Pro Ser Met Ala Met Arg Val Ala Gly Gly Arg Asp Gly Ser
                 85                  90                  95

Cys Leu Pro Val Ala Leu Gly Leu Ala Gly Ala Pro Gln Thr Pro Gly
            100                 105                 110

Val Gly Arg Ala Ile Trp Val Arg Ser Ser Ile Pro Leu Arg Ala Ala
            115                 120                 125

Ser Pro Thr Ser Trp Gly Thr Tyr Arg Ser Ser Ala Pro Leu Leu Glu
        130                 135                 140

Ala Ala Pro Gly Pro Trp Arg Met Ala Ser Gly Phe Trp Lys Thr Ala
145                 150                 155                 160

Thr Met Gln Gln Gly Thr Phe Leu Val Ala Leu Ser Leu Ser Ser Phe
                165                 170                 175

Trp Pro Cys Ser Leu Ala Leu Cys Pro Leu Gln Pro Thr Lys Cys Ala
                180                 185                 190

Ile Pro Arg Gly
        195

<210> SEQ ID NO 3
<211> LENGTH: 13
<212> TYPE: PRT
<213> ORGANISM: Hepatitis C virus
<220> FEATURE:
<221> NAME/KEY: Variant
<222> LOCATION: 8
<223> OTHER INFORMATION: Xaa = Asn or Lys
<220> FEATURE:
<221> NAME/KEY: Variant
<222> LOCATION: 9
<223> OTHER INFORMATION: Xaa = Val or Glu
<220> FEATURE:
<221> NAME/KEY: Variant
<222> LOCATION: 13
<223> OTHER INFORMATION: Xaa = Ala or Val

<400> SEQUENCE: 3

Leu Asn Leu Lys Glu Lys Pro Xaa Xaa Thr Pro Thr Xaa
 1               5                  10

<210> SEQ ID NO 4
<211> LENGTH: 13
<212> TYPE: PRT
<213> ORGANISM: Hepatitis C virus
<220> FEATURE:
<221> NAME/KEY: Variant
<222> LOCATION: 6
<223> OTHER INFORMATION: Xaa = Leu or Ser
<220> FEATURE:
<221> NAME/KEY: Variant
<222> LOCATION: 10
<223> OTHER INFORMATION: Xaa = Ala or Val
<220> FEATURE:
<221> NAME/KEY: Variant
<222> LOCATION: 11
<223> OTHER INFORMATION: Xaa = Ala or Val

<400> SEQUENCE: 4

Ala Ala His Arg Thr Xaa Ser Ser Arg Xaa Xaa Val Arg
 1               5                  10

<210> SEQ ID NO 5
<211> LENGTH: 14

```
<212> TYPE: PRT
<213> ORGANISM: Hepatitis C virus

<400> SEQUENCE: 5

Leu Asn Leu Lys Glu Lys Pro Asn Val Thr Pro Thr Ala Cys
  1               5                  10

<210> SEQ ID NO 6
<211> LENGTH: 14
<212> TYPE: PRT
<213> ORGANISM: Hepatitis C virus

<400> SEQUENCE: 6

Ala Ala His Arg Thr Ser Ser Arg Ala Val Val Arg Cys
  1               5                  10

<210> SEQ ID NO 7
<211> LENGTH: 18
<212> TYPE: PRT
<213> ORGANISM: Hepatitis C virus

<400> SEQUENCE: 7

Pro Thr Asp Pro Arg Arg Arg Ser Arg Asn Leu Gly Lys Val Ile Asp
  1               5                  10                  15

Thr Cys

<210> SEQ ID NO 8
<211> LENGTH: 20
<212> TYPE: PRT
<213> ORGANISM: Hepatitis C virus

<400> SEQUENCE: 8

Gly Cys Ala Thr Arg Lys Thr Ser Glu Arg Ser Gln Pro Arg Gly Arg
  1               5                  10                  15

Arg Ala Pro Ile
            20

<210> SEQ ID NO 9
<211> LENGTH: 195
<212> TYPE: PRT
<213> ORGANISM: Hepatitis C virus

<400> SEQUENCE: 9

Ala Gln Ile Leu Asn Leu Lys Glu Lys Pro Asn Val Thr Pro Thr Ala
  1               5                  10                  15

Ala His Arg Thr Leu Ser Ser Arg Val Ala Val Arg Ser Leu Ala Glu
               20                  25                  30

Phe Thr Cys Cys Arg Ala Gly Ala Pro Asp Trp Val Cys Ala Arg Leu
           35                  40                  45

Gly Arg Leu Pro Ser Gly Arg Ser Leu Val Glu Gly Ala Ser Leu Ser
       50                  55                  60

Pro Arg Ile Ala Gly Pro Arg Ala Gly Pro Gly Leu Ser Pro Gly Thr
 65                  70                  75                  80

Leu Gly Pro Ser Met Ala Met Arg Val Ala Gly Gln Asp Gly Ser
                 85                  90                  95

Cys Pro Pro Ala Ala Leu Gly Leu Leu Gly Ala Pro Met Thr Pro Gly
               100                 105                 110

Gly Gly Pro Ala Ile Trp Val Arg Ser Ser Ile Pro Leu Arg Ala Ala
           115                 120                 125

Ser Pro Thr Ser Trp Gly Thr Ser Arg Ser Ser Ala Pro Leu Gly Ala
```

```
            130             135             140
Ser Pro Glu Leu Trp Arg Met Ala Ser Gly Ser Trp Arg Thr Gly Ile
145                 150                 155                 160

Thr Gln Gln Gly Ile Phe Pro Val Ala Leu Phe Leu Ser Ser Phe Trp
                165                 170                 175

Leu Phe Cys Pro Ala Leu Ser Gln Leu Arg Pro Ser Lys Cys Ala Thr
                180                 185                 190

Leu Val Gly
        195

<210> SEQ ID NO 10
<211> LENGTH: 196
<212> TYPE: PRT
<213> ORGANISM: Hepatitis C virus

<400> SEQUENCE: 10

Ala Arg Ile Leu Asn Leu Lys Glu Lys Pro Asn Val Thr Pro Thr Val
1               5                   10                  15

Ala His Arg Thr Ser Ser Arg Val Ala Val Arg Ser Leu Val Glu
                20                  25                  30

Phe Thr Cys Cys Arg Ala Gly Ala Leu Asp Trp Val Cys Ala Arg Arg
                35                  40                  45

Gly Arg Leu Pro Ser Gly Arg Asn Leu Glu Val Asp Val Ser Leu Ser
50                  55                  60

Pro Arg His Val Gly Pro Arg Ala Gly Pro Gly Leu Ser Pro Gly Thr
65                  70                  75                  80

Leu Gly Pro Ser Met Ala Met Arg Val Ala Gly Gly Arg Asp Gly Ser
                85                  90                  95

Cys Leu Pro Val Ala Leu Gly Leu Ala Gly Ala Pro Gln Thr Pro Gly
                100                 105                 110

Val Gly Arg Ala Ile Trp Val Arg Ser Ser Ile Pro Leu Arg Ala Ala
                115                 120                 125

Ser Pro Thr Ser Trp Gly Thr Tyr Arg Ser Ser Ala Pro Leu Leu Glu
                130                 135                 140

Ala Ala Pro Gly Pro Trp Arg Met Ala Ser Gly Phe Trp Lys Thr Ala
145                 150                 155                 160

Thr Met Gln Gln Gly Thr Phe Leu Val Ala Leu Ser Leu Ser Ser Phe
                165                 170                 175

Trp Pro Cys Ser Leu Ala Leu Cys Pro Leu Gln Pro Thr Lys Cys Ala
                180                 185                 190

Ile Pro Arg Gly
        195

<210> SEQ ID NO 11
<211> LENGTH: 192
<212> TYPE: PRT
<213> ORGANISM: Hepatitis C virus

<400> SEQUENCE: 11

Ala His Phe Leu Asn Leu Lys Glu Lys Pro Lys Glu Thr Pro Ser Val
1               5                   10                  15

Ala His Arg Thr Ser Ser Arg Val Ala Asp Arg Ser Leu Val Glu
                20                  25                  30

Tyr Thr Cys Cys Arg Ala Gly Ala His Asp Trp Val Cys Ala Arg Arg
                35                  40                  45

Val Lys Leu Leu Asn Gly His Ser Leu Ala Asp Asp Ser Leu Ser
```

```
           50                  55                  60
Pro Arg Arg Val Gly Ala Lys Ala Gly Pro Gly Leu Ser Pro Gly Thr
 65                  70                  75                  80

Leu Gly Pro Ser Met Val Thr Arg Ala Ala Gly Gln Gly Gly Gly Ser
                 85                  90                  95

Cys Pro His Ala Ala Pro Val His Pro Gly Ala Gln Met Thr Pro Gly
                100                 105                 110

Gly Gly Pro Ala Ile Trp Val Lys Ser Ser Ile Pro Arg Ala Asp Ser
            115                 120                 125

Pro Thr Ser Trp Gly Thr Ser Arg Gly Gly Ala Leu Leu Glu Ala Ser
            130                 135                 140

Gln Glu Pro Ser Arg Met Ala Gly Pro Leu Lys Thr Gly Ile Ser Gln
145                 150                 155                 160

Gln Gly Thr Cys Pro Val Ala Pro Phe Leu Ser Ser Phe Leu Leu Cys
                165                 170                 175

Ser Leu Ala Phe Ile Gln Gln Pro Val Ser Gly Gly Ile Arg Leu Ala
            180                 185                 190

<210> SEQ ID NO 12
<211> LENGTH: 197
<212> TYPE: PRT
<213> ORGANISM: Hepatitis C virus

<400> SEQUENCE: 12

Ala Gln Ile Leu Asn Leu Lys Glu Lys Pro Lys Glu Thr Gln Thr Ala
 1                   5                  10                  15

Ala His Arg Thr Leu Ser Ser Arg Val Ala Val Arg Ser Leu Ala Glu
                20                  25                  30

Phe Thr Cys Cys Arg Ala Gly Ala Pro Gly Trp Val Cys Ala Arg Gln
             35                  40                  45

Gly Arg Leu Leu Ser Asp Pro Ser Arg Val Asp Asp Ala Ser Pro Ser
 50                  55                  60

Arg Lys Ile Gly Ala Pro Pro Ala Ser Pro Gly Glu Ser Gln Asp Ile
 65                  70                  75                  80

Leu Gly Pro Cys Thr Glu Thr Arg Val Ala Ala Gly Arg Val Gly Ser
                 85                  90                  95

Cys Pro Pro Ala Gly Leu Val Leu Gly Ala Pro Pro Thr Pro Gly
                100                 105                 110

Ile Asp His Ala Ile Trp Ala Glu Ser Ser Ile Pro Leu Arg Val Val
            115                 120                 125

Leu Pro Thr Ser Trp Gly Thr Ser Leu Ser Leu Ala Pro Arg Leu Glu
            130                 135                 140

Ala Ser Pro Glu Leu Trp His Thr Val Leu Gly Ser Trp Arg Thr Gly
145                 150                 155                 160

Ile Thr Gln Gln Gly Ile Tyr Pro Val Ala Leu Phe Leu Ser Phe Cys
                165                 170                 175

Leu Leu Phe Cys His Ala Ser Gln Cys Gln Cys Leu Gln Trp Lys Ser
            180                 185                 190

Gly Thr Leu Val Leu
        195

<210> SEQ ID NO 13
<211> LENGTH: 195
<212> TYPE: PRT
<213> ORGANISM: Hepatitis C virus
```

```
<400> SEQUENCE: 13

Ala Arg Ile Leu Asn Leu Lys Glu Lys Pro Asn Val Thr Pro Thr Ala
1               5                   10                  15

Ala His Arg Thr Leu Ser Ser Arg Val Ala Ala Arg Ser Leu Ala Glu
            20                  25                  30

Phe Thr Cys Cys Arg Ala Gly Ala Pro Glu Trp Val Cys Ala Arg Arg
        35                  40                  45

Gly Arg Leu Pro Ser Gly Arg Asn Leu Ala Gly Val Ser Leu Phe
    50                  55                  60

Pro Arg Pro Ala Asp Pro Arg Glu Gly Pro Gly Arg Ser Pro Gly Thr
65                  70                  75                  80

Leu Gly Pro Ser Met Ala Thr Arg Ala Val Gly Gly Arg Asp Pro Ser
                85                  90                  95

Cys Pro Pro Ala Ala Leu Gly Leu Val Gly Ala Leu Leu Thr Pro Gly
                100                 105                 110

Gly Gly His Ala Ile Trp Val Arg Ser Ser Ile Pro Ser Arg Val Ala
            115                 120                 125

Ser Pro Thr Ser Trp Gly Thr Ser Thr Ser Ser Ala Leu Leu Gly Ala
130                 135                 140

Leu Pro Glu Leu Trp His Met Val Leu Glu Ser Trp Lys Thr Ala Ile
145                 150                 155                 160

Thr Gln Gln Gly Thr Ser Pro Val Ala Leu Phe Leu Ser Ser Cys Ser
                165                 170                 175

Leu Phe Tyr Pro Ala Gln Ser Leu Leu Arg Pro Ser Glu Cys Ala Thr
                180                 185                 190

Leu Arg Gly
        195

<210> SEQ ID NO 14
<211> LENGTH: 194
<212> TYPE: PRT
<213> ORGANISM: Hepatitis C virus

<400> SEQUENCE: 14

Ala Gln Ile Leu Asn Leu Lys Glu Lys Pro Lys Glu Thr Pro Thr Val
1               5                   10                  15
Ala His Lys Thr Leu Ser Phe Arg Ala Ala Arg Ser Leu Ala Glu
            20                  25                  30

Tyr Thr Cys Cys Arg Ala Gly Ala Pro Gly Trp Val Cys Ala Arg Gln
        35                  40                  45

Gly Arg Leu Arg Ser Gly Pro Ser His Val Glu Gly Ala Ser Pro Ser
    50                  55                  60

Leu Arg Ile Gly Ala Pro Leu Ala Asn Pro Gly Glu Asn Gln Asp Thr
65                  70                  75                  80

Pro Gly Pro Tyr Thr Gly Met Arg Asp Ser Ala Gly Gln Asp Arg Ser
                85                  90                  95

Cys Pro Pro Glu Val Pro Val Pro Leu Gly Ala Pro Met Thr Pro Gly
                100                 105                 110

Ile Gly Pro Ala Thr Trp Val Ser Ser Ile Pro Arg Ala Ala Leu
            115                 120                 125

Pro Thr Ser Trp Gly Thr Ser Leu Ser Ala Pro Arg Ser Ala Ala Ser
        130                 135                 140

Pro Glu Leu Ser Arg Met Ala Glu Ser Trp Arg Thr Gly Leu Ile Leu
145                 150                 155                 160

Gln Gln Gly Thr Tyr Pro Val Ala Pro Phe Leu Ser Ser Cys Trp Pro
```

```
                165                 170                 175
Cys Cys Pro Ala Ser Pro Pro Arg Ser Pro Leu Pro Lys Arg Thr Ser
            180                 185                 190
Val Pro
```

<210> SEQ ID NO 15
<211> LENGTH: 194
<212> TYPE: PRT
<213> ORGANISM: Hepatitis C virus

<400> SEQUENCE: 15

```
Ala Gln Ile Gln Asn Pro Lys Asp Lys Pro Lys Glu Thr Pro Thr Val
 1               5                  10                  15
Ala His Arg Thr Ser Ser Ser Arg Ala Val Val Arg Ser Trp Val Glu
            20                  25                  30
Tyr Thr Cys Cys Arg Ala Gly Ala Leu Asp Trp Val Cys Ala Arg Leu
        35                  40                  45
Gly Arg Leu Pro Asn Gly Pro Ser Pro Glu Ala Gly Val Ser Pro Phe
    50                  55                  60
Gln Arg Leu Ala Ala Arg Arg Ala Val Pro Gly Val Ser Leu Gly Thr
65                  70                  75                  80
His Gly Pro Cys Met Gly Met Arg Ala Ala Gly Gly Gln Gly Gly Ser
                85                  90                  95
Cys Pro Pro Ala Ala Leu Ala Gln Arg Gly Ala Gln Thr Thr Pro Gly
            100                 105                 110
Val Gly Leu Ala Thr Trp Val Arg Ser Ser Ile Pro Leu Leu Ala Ala
        115                 120                 125
Ser Pro Thr Trp Gly Thr Ser Pro Ser Ala Ala Pro Gly Ala Ser Gln
    130                 135                 140
Gln Gln Leu Trp Arg Met Ala Ser Gly Leu Leu Arg Thr Gly Ile Met
145                 150                 155                 160
Gln Gln Gly Ile Phe Pro Val Ala Pro Phe Leu Ser Ser Phe Trp His
                165                 170                 175
Phe Phe Arg Ala Leu Tyr Gln Pro Arg Gln Ser Ile Met Pro Ile Arg
            180                 185                 190
Ala Ala
```

<210> SEQ ID NO 16
<211> LENGTH: 195
<212> TYPE: PRT
<213> ORGANISM: Hepatitis C virus

<400> SEQUENCE: 16

```
Ala Arg Ile Leu Asn Leu Lys Glu Lys Pro Asn Val Thr Pro Thr Ala
 1               5                  10                  15
Ala Gln Trp Thr Leu Ser Ser Arg Val Val Ala Arg Ser Leu Ala Glu
            20                  25                  30
Phe Thr Cys Cys Arg Ala Gly Ala Pro Asp Trp Val Cys Ala Arg Leu
        35                  40                  45
Gly Arg Leu Arg Ser Gly Arg Asn Leu Val Glu Asp Ala Asn Leu Ser
    50                  55                  60
Pro Arg Arg Val Asp Pro Arg Glu Gly Pro Gly His Asn Gln Asp Ile
65                  70                  75                  80
His Gly Leu Phe Thr Val Met Arg Val Val Gly Gly Gln Asp Gly Ser
                85                  90                  95
```

-continued

```
Cys Pro Pro Val Ala Leu Asp Arg Leu Gly Ala Gln Met Ile Pro Ala
                100                 105                 110

Gly Gly Pro Ala Ile Trp Val Arg Ser Ser Ile Pro Ala Ala Ser
            115                 120                 125

Pro Thr Ser Trp Asp Thr Ser Arg Ser Ala Pro Pro Trp Val Ala Ser
    130                 135                 140

Pro Gly Pro Trp His Met Val Ser Gly Leu Trp Arg Thr Gly Ser Ile
145                 150                 155                 160

Met Gln Gln Gly Ile Ser Pro Val Ala Pro Phe Leu Ser Ser Trp
                165                 170                 175

His Phe Phe Arg Ala Leu Ser Pro Leu Arg Pro Leu Thr Ile Ala Met
            180                 185                 190

Ser Gln Ala
        195

<210> SEQ ID NO 17
<211> LENGTH: 192
<212> TYPE: PRT
<213> ORGANISM: Hepatitis C virus

<400> SEQUENCE: 17

Ala Gln Ile Leu Asn Leu Lys Glu Lys Pro Asn Val Thr Pro Thr Ala
1               5                   10                  15

Ala His Arg Thr Ser Ser Arg Ala Val Val Arg Ser Leu Val Glu
            20                  25                  30

Phe Thr Cys Cys Arg Ala Gly Ala Pro Gly Trp Val Cys Ala Arg Leu
        35                  40                  45

Gly Arg Leu Pro Ser Gly Arg Asn Leu Val Glu Gly Asp Asn Leu Ser
    50                  55                  60

Pro Arg Phe Ala Gly Pro Arg Ala Gly Pro Gly Leu Ser Pro Gly Thr
65                  70                  75                  80

Leu Gly Pro Ser Met Ala Met Arg Val Trp Gly Gln Asp Gly Ser
                85                  90                  95

Cys His Pro Gly Ala Leu Gly Leu Val Gly Ala Pro Arg Thr Pro Gly
                100                 105                 110

Val Gly Arg Val Ile Trp Val Arg Ser Ser Ile Pro Leu His Ala Gly
            115                 120                 125

Ser Pro Thr Ser Trp Gly Thr Phe Pro Ser Ala Ala Pro Gly Ala Leu
    130                 135                 140

Pro Gly Pro Trp Arg Met Val Ser Gly Phe Trp Arg Ser Ala Thr Thr
145                 150                 155                 160

Gln Gln Gly Phe Pro Val Ala Leu Ser Leu Ser Ser Ser Pro Cys Cys
                165                 170                 175

Pro Val Pro Phe Gln Leu Pro Leu Met Lys Cys Ala Thr Cys Pro Gly
            180                 185                 190
```